(12) United States Patent
Chavas et al.

(10) Patent No.: US 11,135,446 B2
(45) Date of Patent: Oct. 5, 2021

(54) MEDICAL DEVICE INTENDED TO BE WORN IN FRONT OF THE EYES

(71) Applicants: GENSIGHT BIOLOGICS, Paris (FR); Sorbonne Université, Paris (FR); Centre national de la recherche scientifique, Paris (FR); INSTITUT NATIONAL DE LA SANTE ET DE LA RECHERECHE MEDICALE (INSERM), Paris (FR)

(72) Inventors: Joël Chavas, Orsay (FR); Guillaume Chenegros, Trappes (FR); Benjamin Benosman, Pantin (FR)

( * ) Notice: Subject to any disclaimer, the term of this patent is extended or adjusted under 35 U.S.C. 154(b) by 9 days.

(21) Appl. No.: 16/318,435

(22) PCT Filed: Aug. 1, 2017

(86) PCT No.: PCT/EP2017/069425
§ 371 (c)(1),
(2) Date: Jan. 17, 2019

(87) PCT Pub. No.: WO2018/024720
PCT Pub. Date: Feb. 8, 2018

(65) Prior Publication Data
US 2019/0290930 A1   Sep. 26, 2019

(30) Foreign Application Priority Data
Aug. 2, 2016   (EP) ..................................... 16306005

(51) Int. Cl.
*A61F 9/008*   (2006.01)
*A61N 5/06*   (2006.01)
(Continued)

(52) U.S. Cl.
CPC .............. *A61N 5/0622* (2013.01); *A61F 9/08* (2013.01); *A61N 5/062* (2013.01); *G02B 27/017* (2013.01);
(Continued)

(58) Field of Classification Search
CPC .................. A61N 5/0622; A61N 5/062; A61N 2005/005; A61N 2005/0626;
(Continued)

(56) References Cited

U.S. PATENT DOCUMENTS 5,060,062 A   10/1991   Dotson
5,106,179 A   4/1992   Kamaya et al.
(Continued)

OTHER PUBLICATIONS

International Search Report dated Aug. 23, 2017 in International Application No. PCT/EP2017/069425.

*Primary Examiner* — Michael W Kahelin
*Assistant Examiner* — George E Banis
(74) *Attorney, Agent, or Firm* — B. Aaron Schulman, Esq.; Stites & Harbison, PLLC

(57) ABSTRACT

The present invention concerns a medical device (10) intended to be worn by a human wearer, the medical device (10) defining a first area (26) and a second area (28), each area being intended to be positioned in front of a respective eye of the wearer. The medical device (10) comprises a frame (10), comprising a rear shell (34). The rear shell (34) defines a hole (54) facing the first area (26) and the rear shell (34) is opaque facing the second area (28). The medical device (10) also comprises an optical module (20) in the first area (26). The optical module (20) comprises a light source (70) and an optical system (72). The optical module (20) is arranged to send a light beam through the hole (54). The medical device (10) further comprises an electronic circuitry (18), adapted to command the optical module (20).

14 Claims, 3 Drawing Sheets

(51) Int. Cl.
*G02B 27/01* (2006.01)
*G09B 21/00* (2006.01)
*A61F 9/08* (2006.01)
*A61N 5/00* (2006.01)

(52) U.S. Cl.
CPC ....... *G02B 27/0176* (2013.01); *G09B 21/008* (2013.01); *A61N 2005/005* (2013.01); *A61N 2005/0626* (2013.01); *A61N 2005/0648* (2013.01); *G02B 2027/0178* (2013.01)

(58) Field of Classification Search
CPC . A61N 2005/0648; A61F 9/08; G02B 27/017; G02B 27/0176; G02B 2027/0178; G09B 21/008
See application file for complete search history.

(56) References Cited

U.S. PATENT DOCUMENTS

| | | |
|---|---|---|
| 2008/0013037 A1 | 1/2008 | Carollo |
| 2008/0239523 A1 | 10/2008 | Beck et al. |
| 2011/0172653 A1* | 7/2011 | Schneider .......... A61K 38/1767 606/15 |
| 2013/0335543 A1 | 12/2013 | Hilkes et al. |
| 2014/0253866 A1* | 9/2014 | Carabajal ................ G06F 1/203 351/123 |
| 2016/0034252 A1* | 2/2016 | Chabrol ................. G10L 17/26 348/222.1 |
| 2016/0187654 A1* | 6/2016 | Border .................... G02B 5/18 359/567 |
| 2017/0078623 A1 | 3/2017 | Hilkes et al. |

* cited by examiner

MEDICAL DEVICE INTENDED TO BE WORN IN FRONT OF THE EYES

TECHNICAL FIELD OF THE INVENTION

The invention relates to a medical device intended to be worn by a human wearer in front of the wearer's eyes.

BACKGROUND OF THE INVENTION

Optogenetics is based in combining techniques from optic and genetics to control and monitor cell activities. It consists in (i) genetically modifying target cells in order to render them sensitive to light, by the expression of exogenous photoreactive proteins in cellular membrane, and (ii) providing an illuminating device able to provide light to said photoreactive proteins.

It is an extremely powerful tool for selective neuronal activation/inhibition which can, for example, be used to restore neural functions in living animals, including humans (Boyden et al., 2005, *Nature Neuroscience* 8 (9): 1263-68), particularly in the eye (Busskamp et al., 2012, *Gene Therapy* 19 (2): 169-75).

It has been shown that selected wavelengths of light should be close to the optimal wavelengths of the photoreactive proteins (Nagel et al. 2003, *Proceedings of the National Academy of Sciences* 100 (24): 13940-45, Klapoetke et al. 2014, *Nature Methods* 11 (3): 338-46) and that these proteins have a very low sensitivity to light (Asrican et al. 2013, *Front Neural Circuits*, 2013, 7:160; Busskamp et al. 2012, *Gene Therapy* 19 (2): 169-75). Therefore, in order to obtain minimum level of protein activation by light, the intensity of light received by the target cell or protein should be above a minimum value (Barrett et al., 2014, *Visual Neuroscience* 31 (4-5): 345-354).

However, while sufficient light must arrive at the photoreactive proteins to provide its activation, it is required to minimize tissue or cell heat and phototoxicity (Yan et al. 2016, *Vision Research* 121: 57-71). It is further desired to guarantee that the light dose for a given period of time will not cause any tissue or cell damages. Photobiological and ophthalmologic standards setting thresholds for the intensity and for the dose are known in the art (see for example ISO 15004-2 2016; "ISO 62471:2006" 2016; § 8.3 of "ANSI Z136 Standards—LIA" 2014). Intensity is defined as the irradiance (in $mW/mm^2$ or $photons \cdot cm^{-2} \cdot s^{-1}$) and dose in a given period of time is defined as the integral of the intensity over the period of time ($mJ/mm^2$ or $photons \cdot cm^{-2}$).

Thus, it is desirable to provide an illuminating device able to control the intensity of light emitted so that the corresponding dose shall not exceed a maximum value.

Similarly, the eye is itself an optical system with optical aberrations (Navarro, et al. 1998, *Journal of the Optical Society of America A* 15 (9): 2522), which include aberrations like myopia, hypermyopia and astigmatism. Optical aberrations are also present in emmetropic eyes and are taken into account in photobiological and ophthalmologic standards (ISO 15004-2, 2007; ISO 62471, 2006). These aberrations might reduce the light intensity received by photoactivable proteins, accordingly it might be desirable to provide an illuminating device able to at least partially correct these drawbacks.

Currently available illuminating devices adapted to simulate the optogenetic proteins for in vitro experiments have been constructed (Degenaar et al. 2009, *Journal of Neural Engineering* 6 (3): 35007; Grossman et al. 2010, *Journal of Neural Engineering* 7 (1): 16004), but they are not miniaturized and are not yet suited for human use.

Head-Mounted displays are used for augmented reality, for virtual reality or for movie display. However, the light intensity provided by these Head-Mounted Displays is not sufficient and is not configurable to stimulate photoreactive proteins and they therefore are not adapted to optogenetics applications.

Heat produced by the required powerful light source and the control electronics induces a temperature increase that has to be kept within the bounds set by the standard ISO 60601-1 for Medical Electrical Equipment. The device shall also guarantee electrical safety (ISO 60601-1) and electromagnetic compatibility (ISO 60601-1-2, ISO 60601-1-9).

Furthermore, an increase of temperature and of heat transfer of the device in front of the eye may induce dry eye and discomfort. Thus, further temperature constraints are required on the part of the device facing the eye.

It is desirable to provide an illuminating device able to deliver a sufficient light intensity, while maintaining a sufficient level of comfort, particularly in terms of temperature and of weight, for the wearer.

More specifically, it is desirable to provide an illuminating device able to limit excessive thermal energy from the light source and the control electronics and/or to facilitate dissipation of heat, so as to prevent a temperature of the illuminating device from going beyond the maximum temperature of normal operation thereof.

It is further desirable to provide an illuminating device which is miniaturized so that it can be inserted in a device wearable by humans on a daily basis.

SUMMARY OF THE INVENTION

The invention aims at proposing a medical device that is wearable by a user in front of the wearer's eyes during extended periods, without causing excessive discomfort.

To this end, the invention concerns a medical device intended to be worn by a human wearer, the medical device defining a first area and a second area, each of the first area and second being intended to be positioned, when the medical device is worn by a human wearer, in front of a respective eye of the human wearer.

The medical device comprises a frame made in a first material, the frame comprising a rear shell, the rear shell defining a hole facing the first area and the rear shell being opaque facing the second area. The rear shell presents an outer face intended to be facing, when the medical device is worn by a human wearer, the face of the human wearer, and an inner face opposite to the outer face, the hole opening in the inner face and in the outer face.

The medical device further comprises an optical module, the optical module being in the first area and facing the inner face, the optical module comprising a light source and an optical system, the optical module being arranged to send a light beam through the hole.

The medical device also comprises an electronic circuitry, the electronic circuitry being adapted to command the optical module.

According to further aspects of the invention, which are advantageous but not compulsory, the device may include one or several of the following features, taken in any technically admissible combination:

- the frame further comprises a front shell, the front shell being tightly assembled to the rear shell, the front shell presenting an inner face and an outer face, the inner face of the rear shell and the inner face of the front shell defining an internal volume, the optical module and the electronic circuitry being fixed to the front shell and embedded in the internal volume.

the frame defines, in the first area, a first gap between the optical module and the rear shell, and the frame defines, in the second area, a second gap between the electronic circuitry and the rear shell.

the optical module comprises at least a support fixed to the frame in the first area and fixed to the light source and to the optical system, the support defining a first dissipation area on the frame, the support being adapted to evacuate heat produced by the light source to the first dissipation area.

the electronic circuitry comprises a holder plate fixed to the frame in the second area, the holder plate defining a second dissipation area on the frame, the holder plate being adapted to evacuate heat produced by the electronic circuitry to the second dissipation area.

the holder plate and the support are made in a second material, the second material having a thermal conductivity higher than 100 W/m*K.

the holder plate presents a shape adapted to dissipate 3 W of heat with a maximum temperature in the electronic circuitry below 85° C.

the support comprises a support arm, the support arm defining a slot, the light source being embedded in the slot.

the support arm presents a shape adapted to dissipate 3 W of heat produced by the light source, with a maximum temperature in the light source below 65° C.

the light source and the optical system have a total weight below 20 g and occupy a total volume below 10 cm$^3$.

the weight of the frame is below 50 g, and the total weight of the medical device is below 200 g.

the medical device further comprises two arms fixed to the frame for holding the medical device to the head of the wearer, the arms being more flexible than the frame.

each arm is made of a composite material comprising carbon fibers, the thickness of the arm being below 0.9 mm.

the medical device includes a first thermal sensor adapted to measure the temperature in the electronic circuitry and a second thermal sensor adapted to measure the temperature of the light source.

the inner face of the front shell and the inner face of the rear shell present a conductive cover, the conductive cover being made with a conductive material, the electric resistance measured between any two points of the conductive cover using a multimeter being less than 2Ω.

the position of the support arm in the support can be adapted on a per patient basis to the distance between the nose and the pupil of the patient.

BRIEF DESCRIPTION OF THE DRAWINGS

The invention will be better understood on the basis of the following description, which is given only as an illustrative example, without restricting the scope of the invention. The description is given in correspondence with the annexed figures, among which.

DETAILED DESCRIPTION OF EMBODIMENTS

Figure 1:
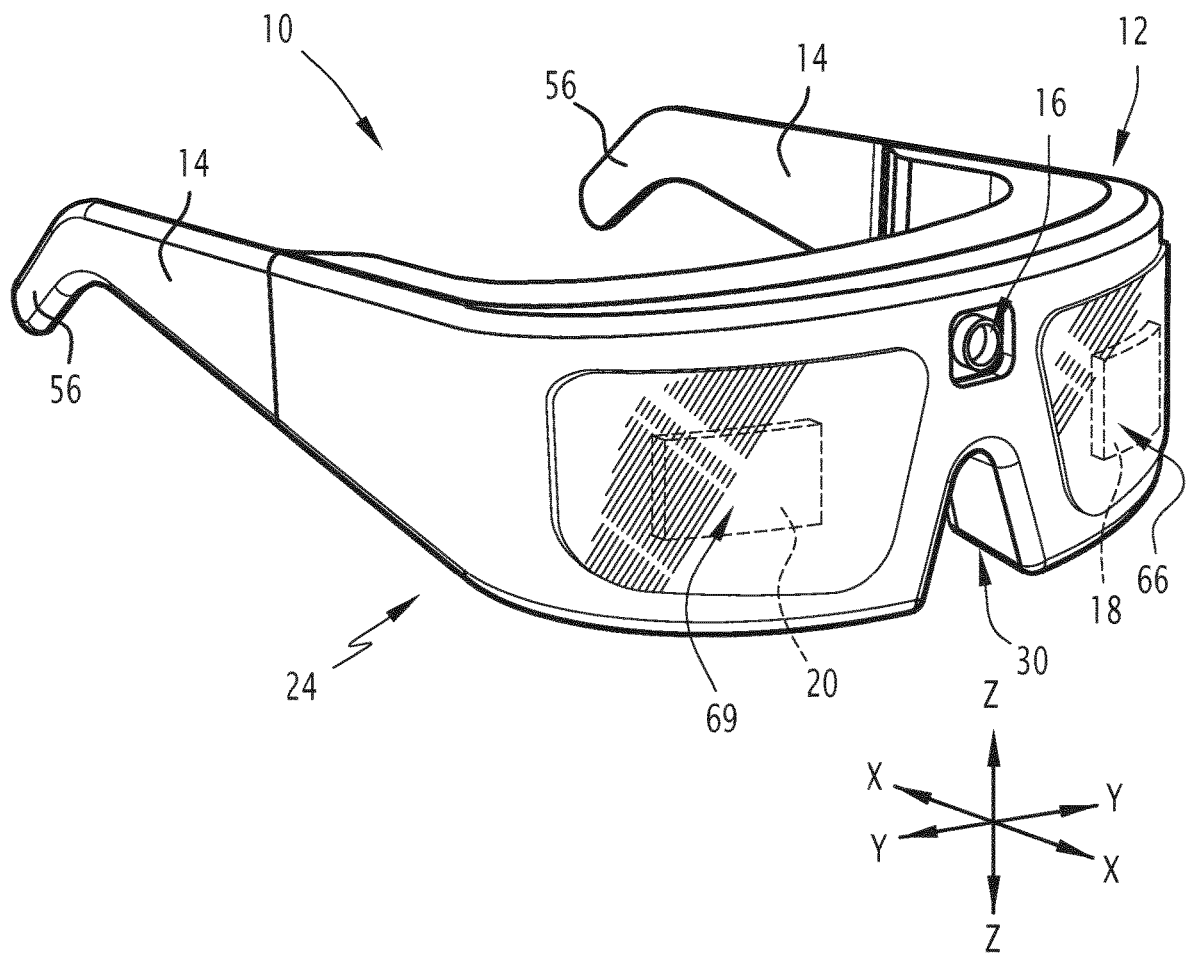
FIG. 1 is a perspective view of a medical device.

A medical device 10, intended to be worn on the head of a human wearer (not represented) in front of their eyes, is represented on FIG. 1.

The medical device 10 is described with relation to a longitudinal axis X-X, a transversal axis Y-Y, and a vertical axis Z-Z.

The longitudinal axis X-X is oriented from a back side to a front side of the head of the human wearing the medical device.

The transversal axis Y-Y is oriented from a left side to a right side of the head of the human wearing the medical device.

The vertical axis Z-Z is oriented from a bottom side to a top side of the head of the human wearing the medical device.

The longitudinal axis X-X, the transversal axis Y-Y and the vertical axis Z-Z are orthogonal to each other.

The medical device 10 is a head-mounted equipment adapted to illuminate at least one eye of the wearer with a controlled light intensity. The medical device 10 is shaped similarly to a pair of glasses.

The medical device 10 comprises a frame 12 fixed to two arms 14 on two respective sides. The medical device 10 also comprises a camera 16, an electronic circuitry 18 and an optical module 20 contained in the frame 12.

The frame 12 is a main body of the medical device 10.

The frame 12 is hollow and defines an internal volume 22 and an external volume 24.

The frame 12 defines a first area 26 and a second area 28 on two respective sides of a median plane X-Z defined by the longitudinal axis X-X and the vertical axis Z-Z.

The frame 12 has a nose slot 30 located in the middle of the frame 12 along the direction of the transversal axis Y-Y.

Figure 2:
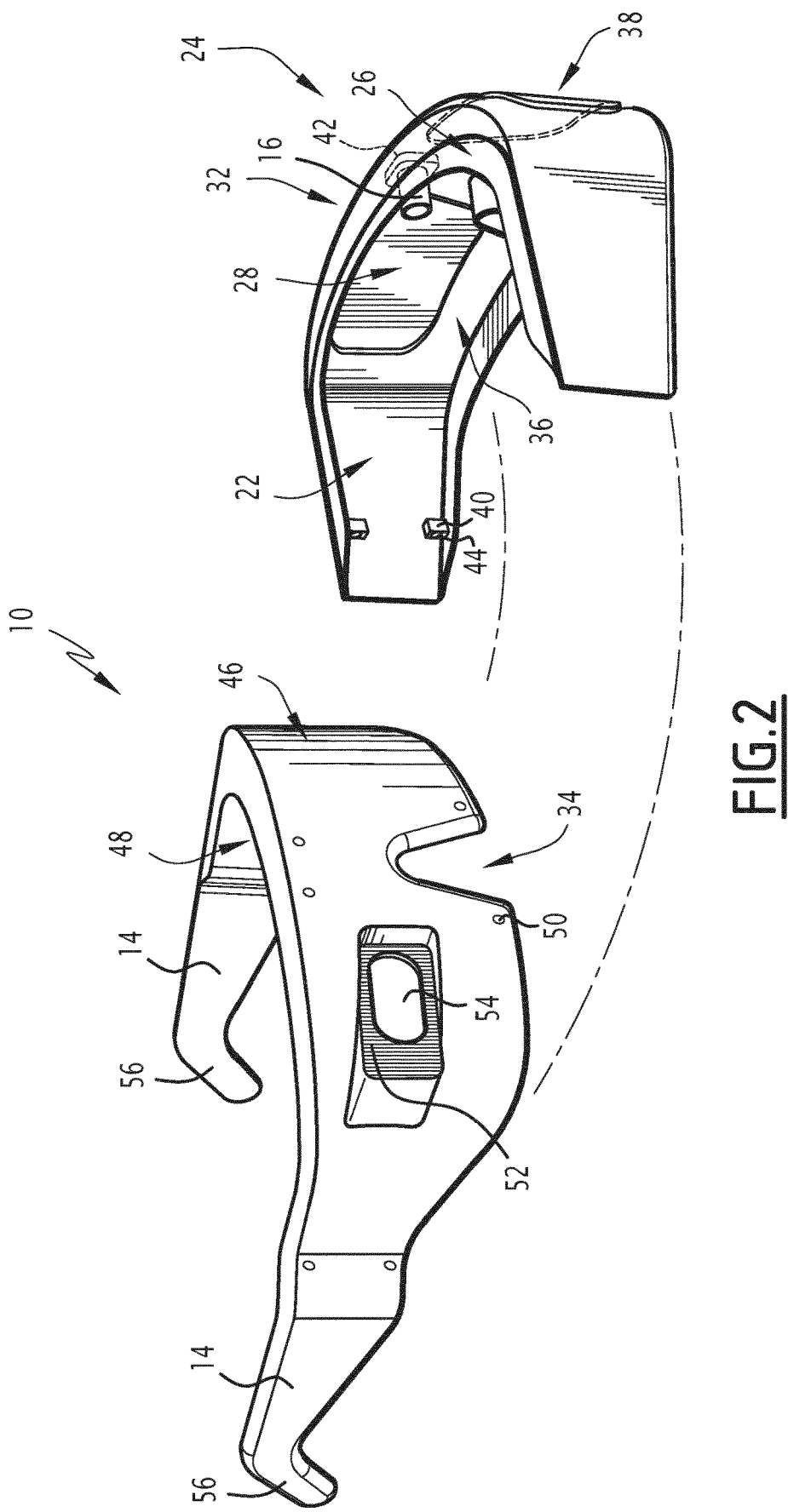
FIG. 2 is an open view of a frame of the device of FIG. 1.

As shown on FIG. 2, the frame 12 comprises a front shell 32 and a rear shell 34. The front shell and the rear shell are assembled to form the frame 12.

The front shell 32 and the rear shell 34 define the internal volume 22.

The frame 12 presents a thickness smaller than 0.9 mm.

The thickness of the frame 12 is the distance separating the internal volume 22 from the external volume 24.

The frame 12 is made of a first material.

The first material has a thermal conductivity higher than 5 W/m*K.

For example, the first material is a composite of carbon fibers and epoxy resin.

Thermal conductivity is a property of a material to conduct heat. It is expressed as a ratio of a heat flux in the material divided by a value of a temperature gradient causing the heat flux.

In the case where the first material presents an anisotropic thermal conductivity, as for some composite materials, the thermal conductivity is higher than 5 W/m*K in at least one direction.

The internal volume 22 is an inner space of the frame 12, defined by the front shell 32 and rear shell 34 when the front shell 32 and the rear shell 34 are assembled.

The internal volume 22 receives the optical module 20 and the electronic circuitry 18, as well as the camera 16.

The first area 26 is a part of the internal volume of the frame 12, on the right side of the median plane X-Z, from the point of view of the wearer.

The first area 26 is adapted to receive the optical module 20. The frame 12 defines a first gap in the first area 26, between the optical module 20 and the rear shell 34.

The first gap is a space containing, for example, air. The first gap thermally isolates the optical module 20, by reducing heat transfers from the optical module towards the rear shell 34.

The second area 28 is a part of the internal volume 22 of the frame 12 on the left side of the median plane X-Z, from the point of view of the wearer.

The second area 28 is adapted to receive the electronic circuitry 18. The frame 12 defines a second gap in the second area 28 between the electronic circuitry 18 and the rear shell 34.

The second gap is a space containing, for example, air. The second gap thermally isolates the electronic circuitry 18, by reducing heat transfers from the electronic circuitry 18 towards the rear shell 34.

The nose slot 30 is a recess in the frame 12. The nose slot 20 is intended to be placed on a nasal bridge of the wearer to support the device 10.

The front shell 32 is a hull made of the first material.

The front shell 32 presents an inner face 36 and an outer face 38, a plurality of filed inserts 40, and an aperture 42 located over the nose bridge 20.

The front shell 32 is opaque.

The inner face of the front shell 36 is a surface of the front shell 32 opposite the outer face of the front shell 38.

The inner face of the front shell 36 is oriented toward the internal volume 22.

The inner face of the front shell 36 is covered with a conductive cover (not represented on the figures).

The conductive cover presents a low electrical resistance.

For example, the resistance of the conductive cover, as measured between any two points of the inner face of the front shell 36 using a multimeter, is smaller than 2Ω.

The cover is, for example, a conductive mesh.

The conductive mesh is a sheet of intercrossing threads made of a conductive material.

The conductive material is a material presenting a low electrical resistivity.

The electrical resistivity of the conductive material is a ratio of a magnitude of an electric field to a magnitude of a current density when an electrical current passes through the conductive material. Thus, the electrical resistance of a material is a measure of the difficulty of passing an electric current through the conductive material.

The electrical resistivity of the conductive material is less than $10^{-7}$ Ω*m.

For example, the conductive material is bronze.

The outer face of the front shell 38 is a surface of the front shell 32 opposite the inner face of the front shell 36.

The outer face of the front shell 38 is oriented toward the external volume 24 of the frame 12.

The filed inserts 40 are fixation posts located on the inner face of the front shell 36.

Each filed insert 40 presents a filed opening 44 oriented toward the rear shell 34, adapted to receive a fixation screw The aperture 42 is a conduit through the front shell 32, linking the internal volume 22 and the external volume 24. The aperture opens in the inner face of the front shell 36 and in the outer face of the front shell 38.

The aperture 42 is adapted to receive the camera 16.

The rear shell 34 is a hull made of the first material, connected to the arms 14 on two opposite sides.

The rear shell 34 presents an inner face 46 and an outer face 48, a plurality of openings 50, and a recess 52 defining a hole 54 facing the first area 26.

The rear shell 34 is opaque facing the second area 28.

The inner face of the rear shell 46 is a surface of the rear shell 34 opposite the outer face of the rear shell 48.

The inner face of the rear shell 46 is oriented toward the internal volume 22.

The inner face of the rear shell 46 is covered with the same conductive cover as the inner face of the front shell 36.

The outer face of the rear shell 48 is a surface of the rear shell 34 opposite the inner face of the rear shell 46.

The outer face of the rear shell 48 is intended to be facing, when the device 10 is worn by a human wearer, the face of the human wearer.

The openings 50 are perforations through the rear shell 34. Each opening 50 is located in order to face one of the filed inserts 40 when the rear shell 34 and the front shell 32 are assembled. Each opening 50 is adapted to receive a fixation screw that continues into the filed opening 44 of the corresponding filed insert 40, in order to assemble the front shell 32 to the rear shell 34.

The recess 52 is a flat panel of the rear shell 34, oriented parallel to the transversal axis Y-Y and to the vertical axis Z-Z.

The recess 52 presents a rectangular shape, facing the first area 26 of the internal volume 22.

The hole 54 is an opening in the middle of the recess 52, facing the first area 26. The hole 54 opens in the inner face of the rear shell 46 and in the outer face of the rear shell 48 of the rear shell 34.

The hole 54 has an oblong cross-section.

The hole 54 is positioned to face the right eye of the wearer when the device 10 is worn.

The hole 54 is adapted to let the beam of light emitted by the optical module 20 pass through, into the right eye of the wearer.

The arms 14 are two branches extending from the rear shell 34 from two respective sides along the transversal axis Y-Y. The arms 14 extend along the longitudinal axis X-X towards the back side of the head of the wearer.

The arms 14 are intended to be worn on the right side and the left side of the head by the wearer, respectively. The arms 14 hold the medical device 10 on the head of the wearer.

Each arm 14 is bent at a respective free end 56, in order to sit on top of a respective ear of the wearer and improve the hold of the device 10.

The arms 14 present a thickness less than 0.9 mm. The thickness of the arm 14 represents a dimension of the arm 14 measured in a direction along the transversal axis Y-Y.

The arms 14 are made of the same first material as the frame 12.

Figure 3:
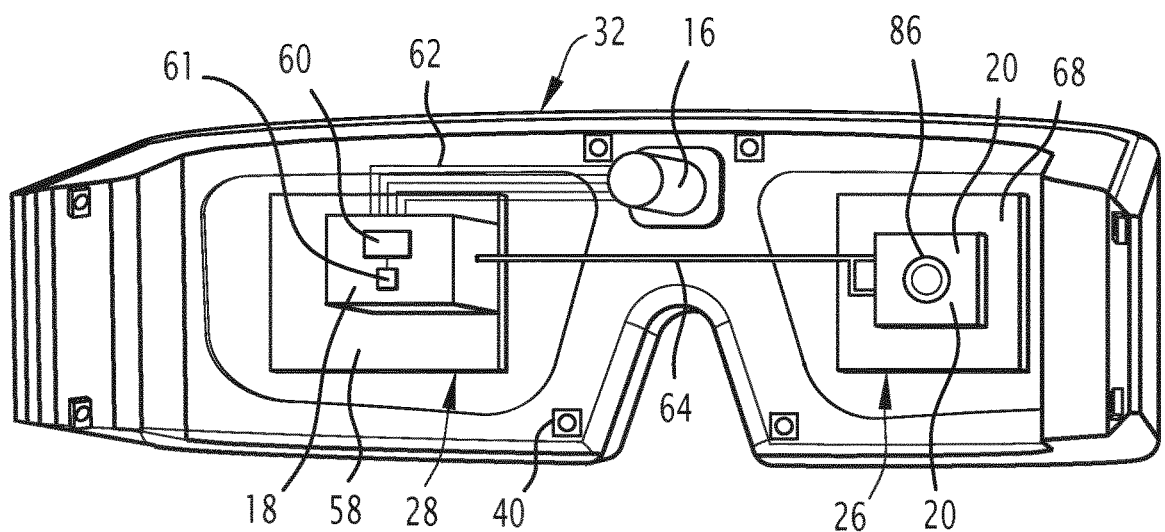
FIG. 3 is a rear view of a front shell of the device of FIG. 1.

The camera 16 is an image acquiring device, shown on FIG. 3. The camera 16 is configured to acquire images of the external volume 24 and convert the images to electronic data.

The camera 16 is positioned in a middle of the internal volume 22 along the transversal axis Y-Y, between the first area 26 and the second area 28.

The camera 16 is embedded in the internal volume 22 and fixed to the front shell 32 facing the aperture 42.

The camera acquires images through the objective.

The objective of the camera crosses the front shell 32 through aperture 42 to emerge above the nose slot 30.

The electronic circuitry 18, shown on FIG. 3, is a group of electronic components.

The electronic circuitry 18 is configured to receive images form the camera 16 in the form of electronic data and to issue commands to the optical module 20.

The electronic circuitry 18 is located in the second area 28. The electronic circuitry 18 is embedded in the internal volume 22.

The electronic circuitry 18 comprises a holder plate 58, a control module 60, a first temperature sensor 61, a first data bus 62 and a second data bus 64.

The holder plate 58 is a support piece adapted to fix the command module 60 to the inner face of the front shell 36 of the front shell 32, in the second area 28.

The holder plate 58 is fixed to the inner face of the front shell with glue.

The glue is an adhesive material presenting a thermal conductivity higher than 2 W/m*K.

The holder plate 58 presents a shape adapted to transmit heat produced by the electronic circuitry 18 to the frame 12.

The holder place 58 presents, for example, a rectangular shape along the transversal Y-Y and vertical Z-Z directions.

In the longitudinal direction X-X, the holder plate 58 is close to the control module 60 on one side, for example within 1 mm of the control module 60 and matches the shape of inner face of the front shell 36 on another side.

The holder plate 58 is made of a second material.

The second material has a thermal conductivity higher than 100 W/m*K.

For example, the second material is aluminium.

The holder plate 58 defines a second dissipation area 66 on the frame 12, represented on FIG. 1.

The second dissipation area 66 is a part of the outer face of the front shell 38 of the front shell 32, located on the left side of the median plane X-Z relative to the wearer.

The second dissipation area 66 faces directly the holder plate 58.

The second dissipation area 66 is in contact with the external volume 24, for example, with air, allowing for a direct thermal exchange.

The second dissipation area 66 is adapted to dissipate heat transmitted by the holder plate 58 to the frame 12 into the external volume 24 when the temperature in the second dissipation area 66 is higher than the temperature in the external volume 24.

The control module 60 is an electronic circuit including at least one electronic chip.

The control module 60 is adapted to analyze images received from the camera 16, to infer commands destined for the optical module 20 and to transfer in real-time data back and forth to an external processing unit.

The control module 60 produces heat when functioning.

The control module 60 produces, for example, 3 W of heat.

The heat produced by the control module 60 is transmitted to the frame 12 by the holder plate 58.

The first temperature sensor 61 is adapted to measure the temperature of the electronic circuitry 18.

The first temperature sensor 61 is, for example, a thermocouple fixed in contact with the holder plate 58.

The first data bus 62 is an electronic cable connecting the camera 16 to the control module 60.

The first data bus 62 is adapted to transmit data, for example, images, from the camera 16 to the control module 60.

The second data bus 64 is an electronic cable connecting the control module 60 to the optical module 20.

The second data bus 64 is adapted to transmit data, for example, electronic commands, from the control module 60 to the optical module 20.

The optical module 20 is a light emitting device, adapted to illuminate the eye of the wearer with a controlled beam of light.

The optical module 20 comprises a support 68, a light source 70, an optical system 72 and a daughterboard 73. The light source 70, the optical system 72 are contained in a closed box. The light source 70, the optical system 72 and the daughter board 73 are represented on FIG. 4.

The support 68 is a holding structure adapted to hold the light source 70, the optical system 72 and the daughterboard 73.

The support 68 is adapted to be fixed to the inner face of the front shell 36 of the front shell 32, in the first area 26.

Figure 4:
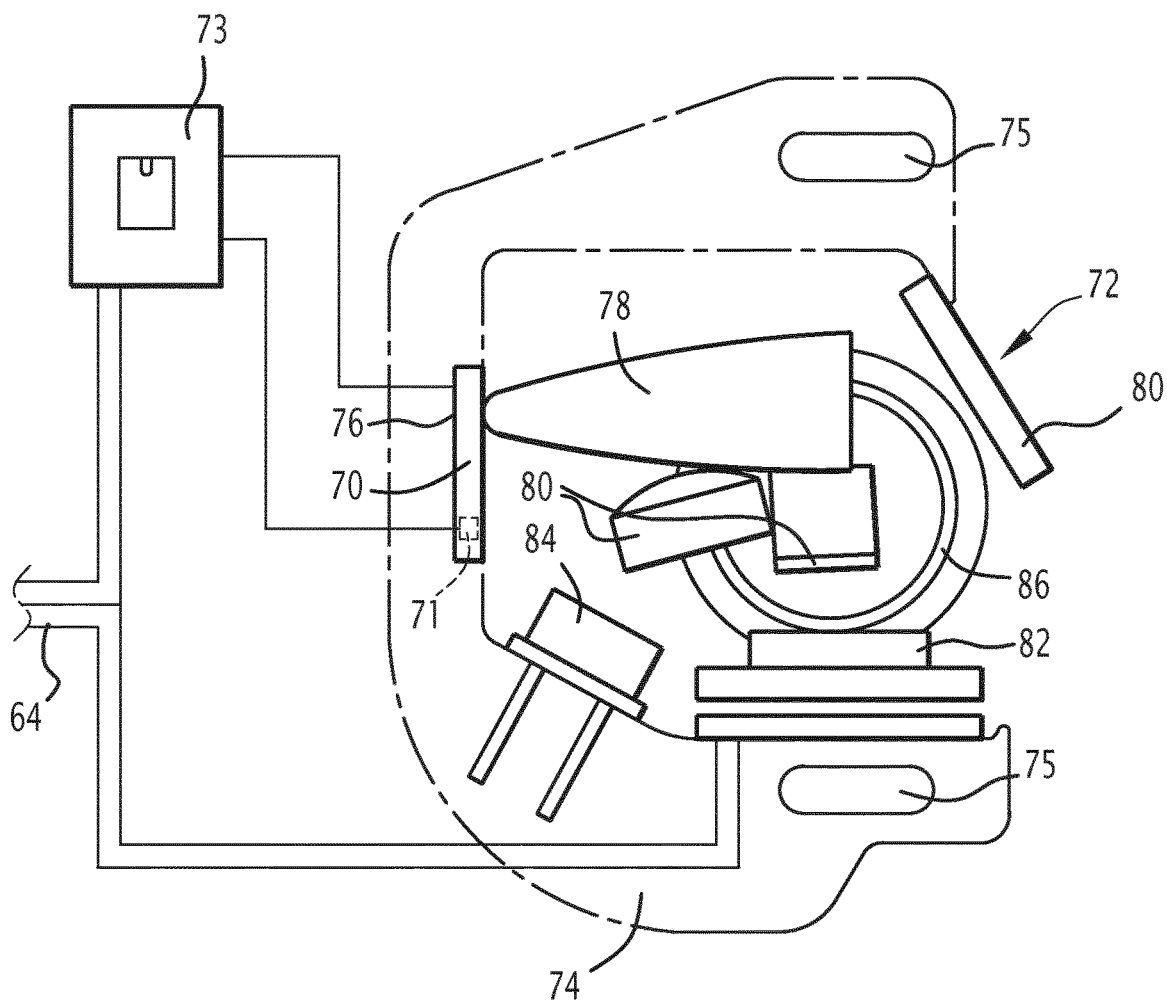
FIG. 4 is a detailed split view of an optical module of the device of FIG. 1.

The support 68 includes a support arm 74, represented on FIG. 4.

The support 68 is made of the second material.

The support 68 defines a first dissipation area 69 on the frame 12, represented on FIG. 1.

The first dissipation area 69 is a part of the outer face of the front shell 38 of the front shell 32, located on the right side of the median plane X-Z relative to the wearer.

The first dissipation area faces directly the support 68.

The first dissipation area 69 is in contact with the external volume 24, for example, with air, allowing for a direct thermal exchange.

The first dissipation area 69 is adapted to dissipate heat transmitted by the support 68 to the frame 12 into the external volume 24 when the temperature in the first dissipation area 69 is higher than the temperature in the external volume 24.

The support arm 74 is a structure adapted to hold the light source 70 and the optical system 72.

The support arm 74 is shaped to maximize the transfer of heat emitted by the light source 70 into the frame 12.

For example, the support arm 74 is shaped like a U to maximize the contact area, with the support 68, which maximizes the transfer of heat to the frame 12 through the support 68.

The support arm 74 presents two holes 75.

The holes 75 are openings in the support arm 74 intended to reduce its weight.

The support arm 74 defines a slot 76.

The slot 76 is a recess in the arm 74, shaped to receive the light source 70. The light source 70 is embedded in the slot 76 to maximize thermal transfers from the light source 70 to the support 68.

The light source 70 is a light-emitting device which converts electric current into light.

The light source 70 comprises a second temperature sensor 71.

The light source 70 is controlled by the daughterboard 73. Notably, the intensity of the light emitted by the light source 70 is controlled by the daughterboard 73.

The light source 70 emits heat when functioning. For example, the light source 70 emits 3 W of heat when emitting light with a maximum intensity.

The light source 70 is embedded in the slot 76 of the support arm 74. The embedment of the light source 70 allows the heat produced by the light source to be transmitted to the support 68.

The light source 70 is, for example, a light emitting diode (LED).

The second temperature sensor 71 is adapted to measure the temperature of the light source 70 and transmit the measured temperature value to the daughterboard 73.

The second temperature sensor 71 is, for example, a thermocouple fixed in contact with a side of the light source 70.

The optical system 72 is a combination of optics adapted to reshape and redirect light.

The optical system 72 is adapted to shape the light emitted by the light source 70 in a controlled beam, and redirect a part of the controlled beam into the eye of the wearer.

The optical system 72 includes a collimator 78, a plurality of mirrors 80, a micro-mirror array 82, a photodiode 84 and a liquid lens 86.

The collimator 78 is an optical device designed to convert an unfocused light beam into a focused beam.

The collimator 78 is adapted to shape a part of the light emitted by the light source 70 into a beam.

The plurality of mirrors includes three mirrors 80. The mirrors 80 are flat light-reflecting surfaces. The mirrors 80 are adapted to redirect the beam of light on a path through the optical system.

The micro-mirror array 82 is a matrix of small mirrors.

Each small mirror of the micro-mirror array 82 is a light-reflecting surface, each dimension of the small mirror being smaller than, for example, 10 µm. Each micro-mirror can be oriented in at least two positions.

The micro-mirror array 82 is adapted to split the beam into a selected part and a rejected part.

The micro-mirrors array is adapted to receive data, for example commands, from the control module 60 through the second data bus 64.

The photodiode 84 is a semiconductor device designed to convert light energy into electric current. The photodiode 84 is adapted to measure the intensity of the rejected part of the beam.

The liquid lens 86 is an adaptable optical device. By adaptable, it is meant that the optical properties of the liquid lens 86 can be easily modified to adapt the medical device 10 to a specific wearer.

The liquid lens 86 is adapted to transmit the selected part of the beam into the eye of the wearer and to be modified in order to correct any optical eye aberration specific to the wearer and to focus the beam on the retina of the wearer.

The daughterboard 73 is an electronic circuit, fixed on the support 68.

The daughterboard 73 is adapted to control the light source 70 and the second temperature sensor 71. Notably, the daughterboard 73 is adapted to control the intensity of the light emitted by the light source 70.

The daughterboard 73 is also adapted to read the temperature values transmitted by the first temperature sensor 61 and the second temperature sensor 71, and to reduce or stop the activity of the device if the temperature values cross preset limits.

The daughterboard 73 is further adapted to receive data, for example commands, from the control module 60 through the second data bus 64.

The functioning of the medical device 10 will now be described.

A human patient, suffering from vision loss due to loss of rod photoreceptors, has been previously treated with a genetic therapy, modifying target cells on the patient's retina to render them sensitive to light.

The medical device 10 is provided, and the liquid lens is adapted to the specific conditions of the patient's eye sight, in order to precisely focus the beam of light on the patient's retina.

The medical device 10 is placed on the face of the patient, with the first area 26 in front of their right eye, and with the second area 28 in front of their left eye.

The camera 16 acquires a picture of the external volume 24, the picture being encoded in the form of electronic data and sent to the control module 60 through the first data bus 62.

The control module 60 analyzes the image and infers a command destined to reproduce the image on the micro-mirror array 82. The command is sent to the optical module 20 through the second data bus 64, and the mirrors of the micro-mirror array 82 are actuated to reproduce the image.

The light source 70 continually emits light, a part of which is shaped into a beam by the collimator 78, then redirected by a first mirror of the plurality of mirrors 80, toward the micro mirror array 82.

The beam is split into a selected part, reproducing the image, and a discarded part.

The selected part is redirected by a second mirror of the plurality of mirrors 80, through the liquid lens 86, into the eye of the patient to form a copy of the image on the retina. The light activates the light-sensitive cells on the patient's retina, allowing the patient to see an approximation of the image.

The discarded part is redirected by a third mirror of the plurality of mirrors 80 onto the photodiode 84. The photodiode 84 measures the light intensity of the discarded part, and the measured value is sent to the daughterboard 73 for regulation of the light intensity.

The daughterboard 73 deduces the light intensity of the selected part of the beam from the light intensity of the discarded part.

The daughterboard 73 then verifies if the light intensity sent into the eye of the patient is within acceptable limits, and changes the intensity of the light emitted by the light source 70 accordingly.

During this process, the electronic circuitry 18 and the light source 70 produce heat, for example 3 W of heat each. An excessive heating of the electronic circuitry 18, and/or of the optical module 20 would compromise an efficient functioning of the device 10, and also cause discomfort for the patient wearing the device 10 on their face, in front of their eyes.

The heat emitted by the electronic circuitry 18 is transmitted to the holder plate 58, which is made of the highly thermal conductive second material. The heat is then transmitted to the frame 12 in the second dissipation area 66.

The heat emitted by the light source 70 is transmitted to the support arm 74, then to the whole support 68, which is made of the highly thermal conductive second material. The heat is then transmitted to the frame 12 in the first second area 69.

The first dissipation area 69 and the second dissipation area 66 are in direct contact with the external volume 24, for example, with air. The heat is thus dissipated in the air of the external volume 24 from the first and second dissipation areas 69, 66, when the temperature of the frame 12 in the first dissipation area 69 or in the second area 66 respectively, is raised higher than the temperature of the external volume 24.

Considering a temperature of the external volume of 25° C. and a heat generation of 3 W for each of the electronic circuitry 18 and the light source 70, the temperature in the electronic circuitry remains below 85° C., and the temperature on the optical module 20 remains below 65° C.

The first and the second gaps isolate the optical module 20 and the electronic circuitry 18 respectively from the rear shell 34. The temperature of the outer face of the rear shell 48, facing the eyes of the wearer, thus does not rise above 35° C. and the medical device 10 remains comfortable for the wearer.

Additionally, the temperature in the parts in contact with the skin of the wearer (the arms 14 and the nose slot 30) does rise by more than 2° C. over an external temperature of the skin, when in contact with the skin of the wearer.

Other temperature constraints on the external part of the device follow the standard ISO 60601-1 (71° C. on upper and lower sides of the front shell 32 and of the rear shell 34, 86° C. on the first dissipation area 66 and second dissipation area 69).

If the temperature of the electronic circuitry 18 measured by the first temperature sensor 61 or if the temperature of the light source 70 measured by the second temperature sensor 71 rises over a preset limit, the daughterboard 73 stops the functioning of the device 10 on order to prevent damage to the device 10 or discomfort to the wearer.

In order to accommodate head size discrepancies between different wearers, the arms 14 are more flexible than the frame 12. This allows the deformation induced by fitting the device 10 on a larger head to be localized in the arms 14 and induce minimal stress in the frame 12. The medical device 10 is thus adapted to fit most wearers without requiring any specific modification of the frame 12 and arms 14.

The connection of the front shell 32 to the rear shell 34 is tight, to prevent passage of external light as well as, for example, water or dust, between the front shell 32 and the rear shell 34. This prevents any damage to the optical module 20, as well as the entry of parasitic light into the internal volume 22.

The conductive mesh on the inner face of the front shell 36 and on the inner face of the rear shell 46 provides electromagnetic shielding to the internal volume 22. Notably, the electromagnetic shielding protects the optical module 20 and the electronic circuitry 18 from parasitic electromagnetic waves from sources located in the external volume 24.

The holder plate 58 is made of the second material which presents a high thermal conductivity. The holder plate 58 also presents a shape adapted to efficiently dissipate heat produced by the electronic circuitry 18 to the second dissipation area 66. This allows keeping a maximum temperature in the electronic circuitry 18 below 85° C. when the electronic circuitry 18 produces 3 W of heat and when the temperature in the external volume 24 is 25° C.

The support 68 is made of the second material which presents a high thermal conductivity. The support 68 also presents a shape adapted to efficiently dissipate heat produced by the light source 70 to the first dissipation area 68. The holder plate 50 presents a shape adapted to dissipate 3 W of heat produced by the light source 70 with a maximum temperature in the light source 70 below 65° C. and the temperature in the external volume 24 of 25° C.

The daughterboard 73 emits very low heat, and thus does not require a specific heat dissipation system.

The optical module 20 is miniaturized, the total mass of the optical module 20, not including the support 68, being, for example, less than 20 g. The volume of the optical module 20, defined as the volume occupied by the closed box containing the light source 70 and the optical system 72, inside the internal volume 22, is less than, for example, 10 cm$^3$.

The plurality of mirrors 80 allows for a reduced volume of the optical module 20, by folding the path of the beam between the different elements constituting the optical system 72.

The medical device 10 is intended to be used with an external unit comprising notably batteries, to supply electrical power to the camera 16, the electronic circuitry 18 and the optical module 20. This allows for a large reduction in the weight of the device 10, as the external unit can be worn in the wearer's pocket and connected to the medical device 10 by a power cord.

Additionally, as a variant, the external unit includes data processing systems, adapted to execute a part of the analysis of the images transmitted by the camera 16 in lieu of the command module 60, as well as to store data.

As another variant, the nose slot 20 comprises at least one nose pad for increased comfort for the wearer.

As another variant, the filed inserts 40 are located on the rear shell 34 and the openings 50 are located on the front shell 32.

As another variant, a joint is located on an inner edge of the front shell 32, in order to be squeezed against the inner face of the rear shell 46 of the rear shell 34 when the front shell 32 is connected to the rear shell 34.

As another variant, each arm 14 presents at least one stud at the free end 56. The studs can be used to fix removable fillers on the arms 14 to adapt the device 10 to a wearer with a small head.

The invention claimed is:

1. A wearable medical device, the medical device defining a first area and a second area, each of the first area and second areas positioned, when the medical device is worn by a human wearer, in front of a respective eye of the human wearer, the medical device comprising:
   a frame made in a first material, the frame comprising a rear shell, the rear shell defining a hole facing the first area and the rear shell being opaque facing the second area,
   the rear shell presenting an outer face intended to be facing, when the medical device is worn by a human wearer, the face of the human wearer, and an inner face opposite to the outer face, the hole opening in the inner face and in the outer face,
the medical device further comprising:
   an optical module, the optical module being in the first area and facing the inner face, the optical module comprising a light source and an optical system, the optical module being arranged to send a light beam through the hole,
   an electronic circuitry, the electronic circuitry being adapted to command the optical module;
   wherein the frame further comprises a front shell, the front shell being tightly assembled to the rear shell, the front shell presenting an inner face and an outer face, the inner face of the rear shell and the inner face of the front shell defining an internal volume, the optical module and the electronic circuitry being fixed to the front shell and embedded in the internal volume;
   wherein the light source and the optical system are contained in a closed box;
   wherein the frame defines, in the first area, a first gap between the optical module and the rear shell; and
   wherein the front shell is opaque facing the first area and facing the second area.

2. The medical device according to claim 1, wherein the frame defines, in the second area, a second gap between the electronic circuitry and the rear shell.

3. The medical device according to claim 1, wherein the optical module comprises at least a support fixed to the frame in the first area and fixed to the light source and to the optical system, the support defining a first dissipation area on the frame, the support being adapted to evacuate heat produced by the light source to the first dissipation area.

4. The medical device according to claim 1, wherein electronic circuitry comprises a holder plate fixed to the frame in the second area, the holder plate defining a second dissipation area on the frame, the holder plate being adapted to evacuate heat produced by the electronic circuitry to the second dissipation area.

5. The medical device according to claim 4,
wherein the optical module comprises at least a support fixed to the frame in the first area and fixed to the light source and to the optical system, the support defining a first dissipation area on the frame, the support being adapted to evacuate heat produced by the light source to the first dissipation area and
wherein the holder plate and the support are made in a second material, the second material having a thermal conductivity higher than 100 W/m*K.

6. The medical device according to claim 5, wherein the holder plate presents a shape adapted to dissipate 3 W of heat with a maximum temperature in the electronic circuitry below 85° C.

7. The medical device according to claim 5, wherein the support comprises a support arm, the support arm defining a slot, the light source being embedded in the slot.

8. The medical device according to claim 7, wherein the support arm presents a shape adapted to dissipate 3 W of heat produced by the light source, with a maximum temperature in the light source below 65° C.

9. The medical device according to claim 1, wherein the light source and the optical system have a total weight below 20 g and occupy a total volume below 10 cm³.

10. The medical device according to claim 1, wherein the weight of the frame is below 50 g, and wherein the total weight of the medical device is below 200 g.

11. The medical device according to claim 1, wherein the medical device further comprises two arms fixed to the frame for holding the medical device to the head of the wearer, the arms being more flexible than the frame.

12. The medical device according to claim 11, wherein each arm is made of a composite material comprising carbon fibers, the thickness of the arm being below 0.9 mm.

13. The medical device according to claim 1, wherein the medical device includes a first thermal sensor adapted to measure the temperature in the electronic circuitry and a second thermal sensor adapted to measure the temperature of the light source.

14. The medical device according to claim 1, wherein the inner face of the front shell and the inner face of the rear shell present a conductive cover, the conductive cover being made with a conductive material, the electric resistance measured between any two points of the conductive cover using a multimeter being less than 2Ω.

* * * * *